(12) United States Patent  
Dalke (10) Patent No.: US 9,060,703 B2
(45) Date of Patent: Jun. 23, 2015

(54) NEUROPHYSIOLOGICAL DRY SENSOR (75) Inventor: Dale Dalke, Thousand Oaks, CA (US)

(73) Assignee: NEUROTOPIA, INC., Atascadero, CA (US)

( * ) Notice: Subject to any disclaimer, the term of this patent is extended or adjusted under 35 U.S.C. 154(b) by 349 days.

(21) Appl. No.: 13/551,917

(22) Filed: Jul. 18, 2012

(65) Prior Publication Data

US 2014/0024912 A1   Jan. 23, 2014

(51) Int. Cl.
*A61B 5/0478*   (2006.01)

(52) U.S. Cl.
CPC ....... *A61B 5/0478* (2013.01); *A61B 2562/0209* (2013.01); *A61B 2562/125* (2013.01); *A61B 2562/164* (2013.01)

(58) Field of Classification Search
CPC ...................................... A61B 5/0478
USPC ................................. 600/383, 544
See application file for complete search history.

(56) References Cited

U.S. PATENT DOCUMENTS

| 4,550,735 | A | * | 11/1985 | Akamatsu et al. ............ 600/386 |
| 4,928,704 | A | | 5/1990 | Hardt |
| 4,967,038 | A | | 10/1990 | Gevins et al. |
| 5,899,867 | A | | 5/1999 | Collura |
| 6,254,536 | B1 | | 7/2001 | DeVito |
| 6,450,820 | B1 | | 9/2002 | Palsson et al. |
| 6,996,261 | B2 | | 2/2006 | deCharms |
| 7,983,762 | B2 | | 7/2011 | Gliner et al. |
| 8,731,633 | B2 | * | 5/2014 | Asjes et al. ................... 600/383 |
| 2009/0069707 | A1 | | 3/2009 | Sandford |
| 2009/0156925 | A1 | | 6/2009 | Jin et al. |
| 2009/0216140 | A1 | | 8/2009 | Skrabal |
| 2009/0281408 | A1 | | 11/2009 | Lee et al. |
| 2010/0198042 | A1 | * | 8/2010 | Popescu et al. ............... 600/383 |
| 2010/0217099 | A1 | | 8/2010 | LeBoeuf et al. |
| 2011/0054288 | A1 | * | 3/2011 | Besio ............................ 600/386 |
| 2011/0054342 | A1 | | 3/2011 | Matthews, Jr. |
| 2011/0054649 | A1 | | 3/2011 | Sarkis et al. |
| 2011/0183305 | A1 | | 7/2011 | Orbach |
| 2011/0270074 | A1 | | 11/2011 | deCharms |
| 2012/0021394 | A1 | | 1/2012 | deCharms |
| 2012/0071947 | A1 | | 3/2012 | Gupta et al. |
| 2012/0077160 | A1 | | 3/2012 | DeGutis et al. |
| 2012/0092618 | A1 | | 4/2012 | Yoo et al. |
| 2012/0100514 | A1 | | 4/2012 | Desain et al. |
| 2012/0130205 | A1 | | 5/2012 | Burton et al. |

FOREIGN PATENT DOCUMENTS

WO    00/56211    9/2000

OTHER PUBLICATIONS

PCT International Search Report, Application No. PCT/US2013/051005, Applicant: Neurotopia, Inc., Apr. 21, 2014, pp. 1-16.

* cited by examiner

*Primary Examiner* — Lee S Cohen (74) *Attorney, Agent, or Firm* — Hall Estill Attorneys at Law; Daniel P. Dooley (57) ABSTRACT

Preferably, an embodiment of a sensor assembly includes at least a sensor probe assembly providing a plurality of conductive pins, a compressible electrically conductive member in electrical communication with the sensor probe assembly, and a signal processing circuit in electrical communication with the compressible electrically conductive member. Preferably, the sensor assembly of the preferred embodiment further includes at least a housing confining said sensor probe assembly, compressible electrically conductive member, and signal processing circuit to form said sensor assembly.

14 Claims, 10 Drawing Sheets

NEUROPHYSIOLOGICAL DRY SENSOR

FIELD OF THE INVENTION

The present invention relates to the field of sensors. More particularly, the present invention relates to dry sensors for use in collecting brainwave data from subjects.

BACKGROUND OF THE INVENTION

The present invention relates to dry sensors for use in recording neurophysiological signals from subjects. Prior art sensor probe assemblies, have for the most part, depended on the preparation of an area of interest on a cranium of a subject, application of a gel like conductive material, and attachment of the probe to the cranium of the subject at the prepared and gelled site.

As advancements have been made in the field of electronics, it has become desirable to obtain neurophysiological signal data from subjects external to a laboratory or testing facility environment, without the need to prepare and apply a gel to a site of interest. Accordingly, improvements in apparatus and methods of providing dry sensors are needed and it is to these needs the present invention are directed.

SUMMARY OF THE INVENTION

In accordance with preferred embodiments, an electrically conductive member in electrical communication with a plurality sensor probe assembly, wherein each sensor probe assembly provides a plurality of conductive pins, a signal processing circuit in electrical communication with said plurality of conductive pins, and a brainwave processing system communicating with said signal processing circuit is provided.

In an alternate preferred embodiment, a sensor assembly includes at least a differential amplifier interacting with said printed circuit member, a reference signal communicating with said differential amplifier, a subject signal provided by said sensor probe assembly, when said sensor probe assembly is in electrical contact with a cranium of a subject, and wherein said differential amplifier compares said reference signal to said subject signal and discards common signal patterns presented by said reference and subject signals to provide a native brainwave signal of the subject.

The alternate preferred embodiment further preferably includes at least an analog to digital converter with a digital signal processing core interacting with said differential amplifier and processing said native brainwave signal provided by said differential amplifier and outputting a digital signal representative of said native brainwave signal, an infinite impulse response filter interacting with said analog to digital converter to serve as a band pass filter for said digital signal, a memory communicating with said processor and storing a plurality of native brainwave signals, and a communication port communicating with the memory and responsive to the processor for communicating native brainwave to the brainwave processing system.

These and various other features and advantages that characterize the claimed invention will be apparent upon reading the following detailed description and upon review of the associated drawings.

BRIEF DESCRIPTION OF THE DRAWINGS

The present invention is illustrated by way of example and not limitation in the figures of the accompanying drawings, in which like references indicate similar elements and in which:

FIG. 9 is a front elevation view of an embodiment exemplary of an electrically conductive pin of FIG. 6, showing a head portion, a tip portion, and a body portion disposed there between.

FIG. 10 is a front elevation view of an embodiment exemplary of an electrically conductive pin of FIG. 2, showing a head portion having a convex shape, a tip portion, and a body portion disposed there between.

FIG. 11 is a front elevation view of an alternate embodiment exemplary of an electrically conductive pin of FIG. 2, showing a head portion having a concave shape, a tip portion, and a body portion disposed there between.

FIG. 12 is a front elevation view of an embodiment exemplary of an electrically conductive pin of FIG. 2, showing a head portion having a substantially flat top surface, a tip portion, and a body portion disposed there between.

DESCRIPTION OF PREFERRED EMBODIMENTS

It will be readily understood that elements of the present invention, as generally described and illustrated in the figures herein, could be arranged and designed in a wide variety of different configurations. Referring now in detail to the drawings of the preferred embodiments, a sensor probe assembly 10, of FIG. 1, (also referred to herein as assembly 10) of a first preferred embodiment, while useable for a wide variety of biophysiological sensing applications, it is particularly adapted for use as neurophysiological signal sensor component. Accordingly, the assembly 10 of the first preferred embodiment, of FIG. 1, will be described in conjunction with the merits of the use of the sensor probe assembly 10 as a neurophysiological signal sensor component. Preferably, the sensor probe assembly 10 is removable, replaceable, interchangeable, and disposable.

Figure 1:
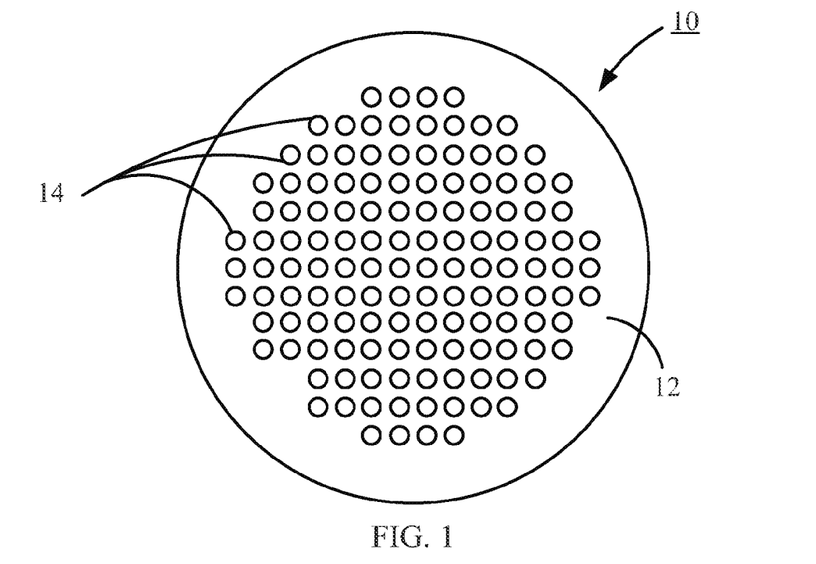
FIG. 1 is a top plan view of an embodiment exemplary of the inventive sensor probe assembly.
Figure 3:
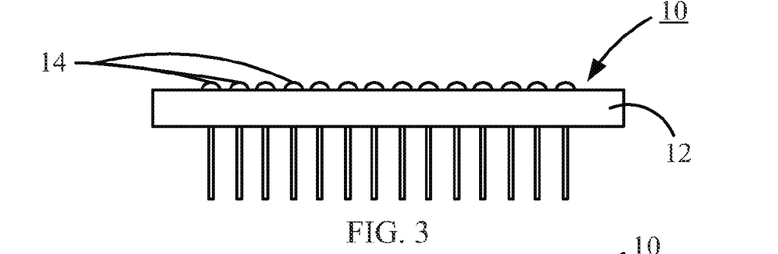
FIG. 3 is a front side view in elevation of an embodiment exemplary of the inventive sensor probe assembly of FIG. 1.

In a preferred embodiment of FIG. 1, the sensor probe assembly 10 includes at least a conductive pin securement member 12, which hosts a plurality of conductive pins 14. Preferably, the plurality of conductive pins 14 are electrically conductive, and when in pressing contact with the conductive pin securement member 12, as shown by FIG. 3, form the sensor probe assembly 10 that yields a low impedance neurophysiological signal sensor component.

Figure 2:
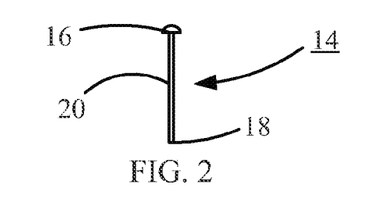
FIG. 2 is a view in elevation of an embodiment exemplary a conductive pin of the inventive sensor probe assembly of FIG. 1.

In a preferred embodiment, the conductive pins 14, an example of which is shown by FIG. 2, include at least a head portion 16, a tip portion 18, and a body portion 20 disposed between the head portion 16 and the tip portion 18. Preferably, each conductive pin 14 is formed from a non-corrosive material, such as stainless steel, titanium, bronze, or a gold plating on a rigid substrate selected from a group including at least polymers and metals. Preferably, the head portion 16 has a diameter greater than the diameter of the body portion 20.

Figure 4:
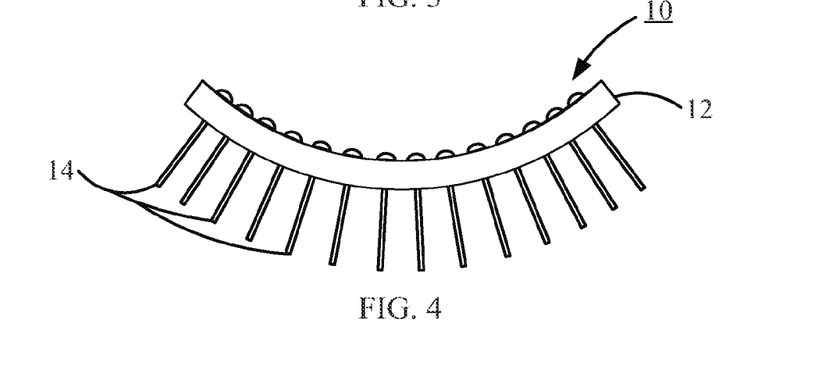
FIG. 4 is a front side view in elevation of an embodiment exemplary of the inventive sensor probe assembly illustrative of a flexible, electrically conductive pin securement member and associated plurality of electrically conductive pins matted thereto, of an embodiment exemplary of the inventive sensor probe assembly of FIG. 1.

As shown by FIG. 4, the conductive pin securement member 12 is preferably flexible and formed from a polymer. The electrical conductivity of the conductive pin securement member 12 is preferably attained by the inclusion of conductive particles embedded within the polymer. One such combination is a carbon filled silicon sheet material provided by Stockwell Elastomerics, Inc. of Philadelphia, Pa. However, as known in the art, conductive polymers may be formed from a plurality of polymer materials filled with conductive particles, the shape of which may be formed using well known manufacturing techniques that include at least molding, extrusion dies and sliced to thickness, formed in sheets and: die cut; cut with hot wire equipment; high pressure water jets, or steel rule dies.

Figure 5:
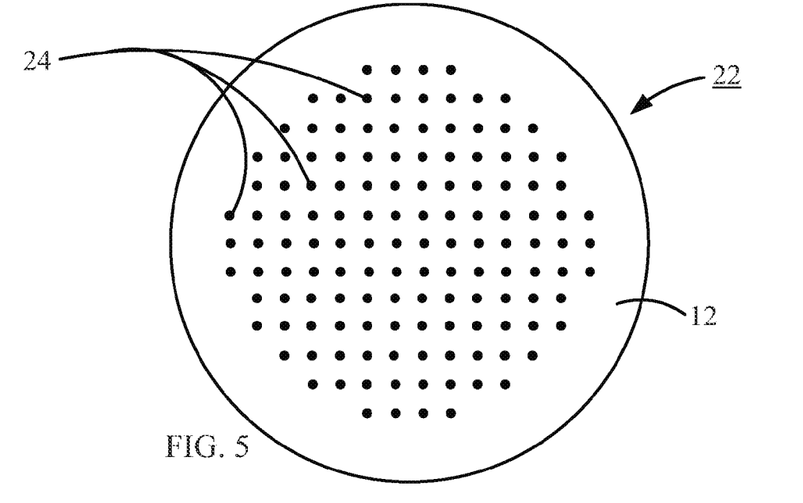
FIG. 5 is a top plan view of an alternate embodiment exemplary of the inventive sensor probe assembly.
Figure 6:
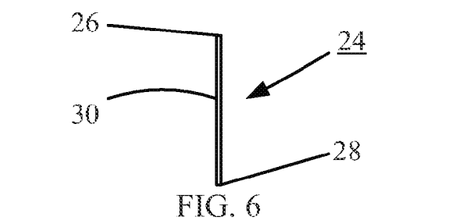
FIG. 6 is a view in front elevation of an alternate embodiment exemplary of an electrically conductive pin of the inventive sensor probe assembly of FIG. 5.

FIG. 5 shows an alternate embodiment of a sensor probe assembly 22, which is preferably formed from the conductive pin securement member 12, and a plurality of alternate preferred conductive pins 24. As shown by FIG. 6, preferably each alternate preferred conductive pin 24 includes a head portion 26, a tip portion 28, and a body portion 30, wherein the head portion 26 and the tip portion 28 have diameters substantially equal to the body portion 30. However, a skilled artisan will appreciate that conductive pins may have head, tip and body portion diameters different from one another. For example, the body portion may have a diameter greater than either the tip portion or head portion to accommodate insert molding of the conductive pins into a conductive pin securement member. It is further understood that the conductive pins may take on a profile that includes a bend in the body, tip, or head portions, as opposed to the cylindrical configuration of any suitable cross section geometric shape of the conductive pins shown by FIG. 2 and FIG. 6. It is still further understood, that the conductive pins may be formed by a plurality of individual components, including without limitation a spring, or may be formed from a coiled or other form of spring alone.

As with the preferred conductive pins 14, the alternate preferred conductive pins 24 are formed from a non-corrosive material, such as stainless steel, titanium, bronze, or a precious metal plating on a rigid substrate selected from a group including at least polymers and metals.

Figure 7:
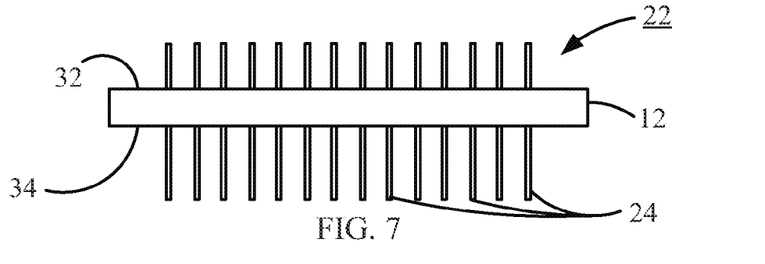
FIG. 7 is a front side view in elevation of an alternate embodiment exemplary of the inventive sensor probe assembly of FIG. 5.
Figure 8:
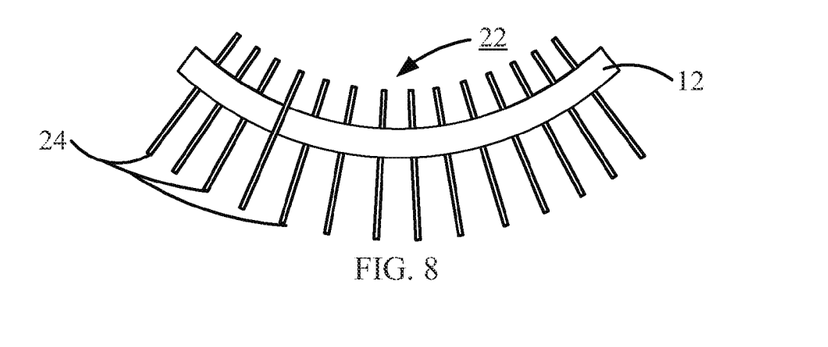
FIG. 8 is a front side view in elevation of an alternate embodiment exemplary of the inventive sensor probe assembly illustrative of a flexible, electrically conductive pin securement member and associated plurality of electrically conductive pins matted thereto, of an embodiment exemplary of the inventive sensor probe assembly of FIG. 5.
Figure 9:
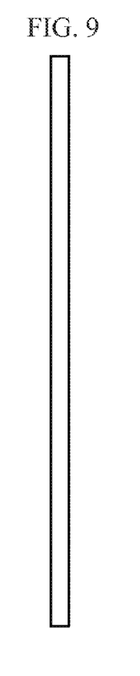
Figure 10:
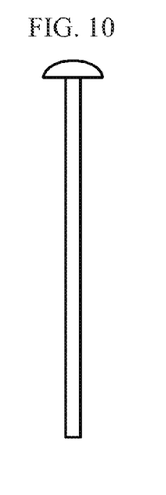
Figure 11:
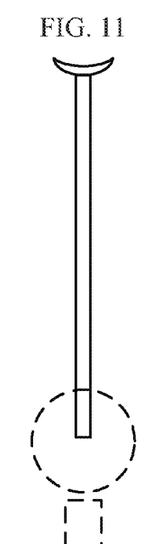
Figure 12:
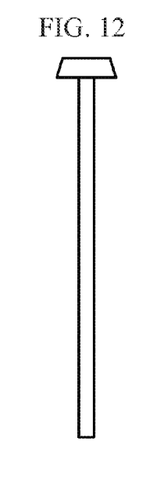

FIG. 7 shows the conductive pins 24 protruding through each the top and bottom surfaces, 32 and 34 respectfully, to accommodate improved conductivity of the alternate sensor probe assembly 22, with mating components. While FIG. 8 shows that the alternate sensor probe assembly 22 preferably retains the flexibility characteristics of sensor probe assembly 10 of FIG. 4.

FIGS. 9, 10, 11, and 12 show just a few of a plurality of head configurations suitable for use on conductive pins. The particular configuration selected is a function of the device or component with which the conductive pins electrically cooperate. When a connector is used to interface with the sensor probe assembly, such as 10 or 22, the precise configuration will depend on the type and configuration of the pins associated with the connector, including whether the pins are male or female pins.

Figure 13:
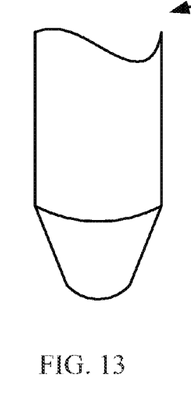
FIG. 13 is a partial cutaway front elevation view of an alternate tip configuration for any of the electrically conductive pins of FIG. 9, 10, 11, or 12.
Figure 14:
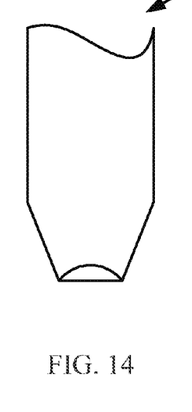
FIG. 14 is across-section, partial cutaway front elevation view of an alternate tip configuration for any of the electrically conductive pins of FIG. 9, 10, 11, or 12.
Figure 15:
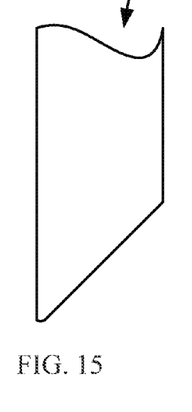
FIG. 15 is a partial cutaway front elevation view of an alternative tip configuration for any of the electrically conductive pins of FIG. 9, 10, 11, or 12.
Figure 16:
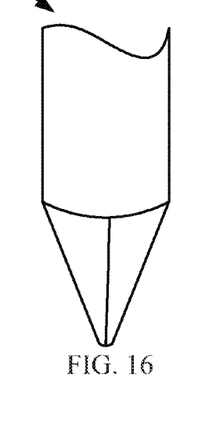
FIG. 16 is a partial cutaway front elevation view of an alternate tip configuration for any of the electrically conductive pins of FIG. 9, 10, 11, or 12.

FIGS. 13, 14 (a cross section view), 15, and 16 show just a few of a plurality of tip configurations suitable for use on conductive pins. The particular configuration selected is a function of the materials used to form the conductive pins, and the environment in which the conductive pin will be placed. Examples of the use environment include where on the cranium the sensor will be placed, whether hair is present, and the sensitivity of the subject to the tips of the conductive pins.

Figure 17:
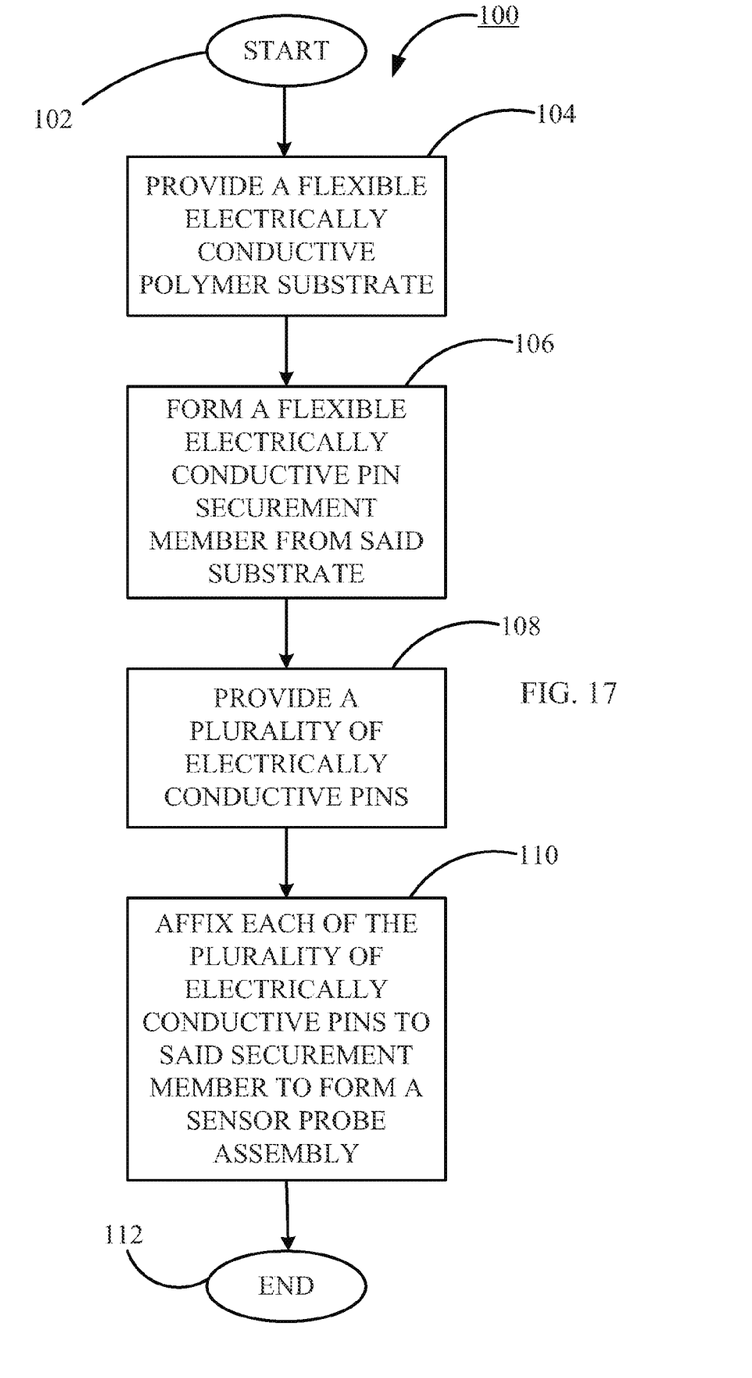
FIG. 17 is a flowchart of a method of producing an embodiment exemplary of the inventive sensor probe assembly of either FIG. 1 or FIG. 5.

FIG. 17 shows a method 100, of making a sensor probe assembly, such as 10 or 22. The method begins at start step 102, and proceeds to process step 104, where a flexible conductive pin securement material is provided (also referred to herein as a flexible, electrically conductive, polymer substrate). At process step 106, a flexible, electrically conductive, pin securement member such as 12) is formed from the flexible, electrically conductive, polymer substrate.

The process continues at process step 108, a plurality of electrically conductive pins (such as 14) is provided. At process step 110, each of the plurality of electrically conductive pins are affixed to the flexible, electrically conductive, pin securement member, and the process concludes at end process step 112 with the formation of a sensor probe assembly.

Figure 18:
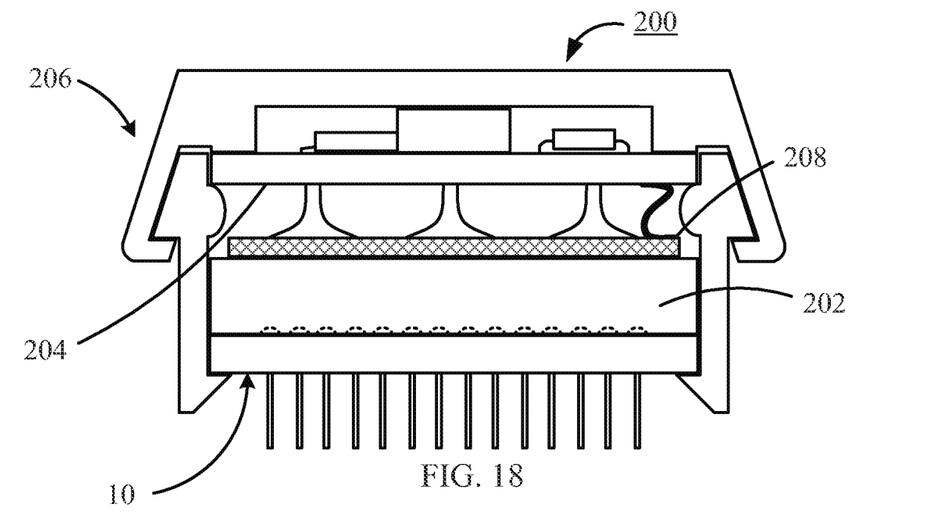
FIG. 18 is a front elevation view of an embodiment exemplary of the present novel sensor assembly.

Turning to FIG. 18, shown therein is an embodiment of a novel, inventive, sensor assembly 200. Preferably, the sensor assembly 200 includes at least a sensor probe assembly 10, which provides a plurality of conductive pins 14, and a compressible electrically conductive member 202, in electrical communication with the sensor probe assembly. Preferably, the compressible electrically conductive member 202 is formed from a polyurethane polymer filled with conductive particles, which are preferably carbon particles. One such combination is a low density black conductive Polyurethane open cell flexible conductive foam material provided by Correct Products, Inc. of Richardson, Tex. However, as known in the art, conductive polymers may be formed from a plurality of polymer materials filled with conductive particles, the shape of which may be formed using well known manufacturing techniques that include at least molding, extrusion dies and sliced to thickness, formed in sheets and: die cut; cut with hot wire equipment; high pressure water jets, or steel rule dies.

As further shown by FIG. 18, the embodiment of the novel, inventive, sensor assembly 200 includes at least a signal processing circuit 204, in electrical communication with the compressible electrically conductive member 202, and a housing 206, confining the sensor probe assembly 10, the compressible electrically conductive member 202, and the signal processing circuit 204, to form the sensor assembly 200.

Figure 19:
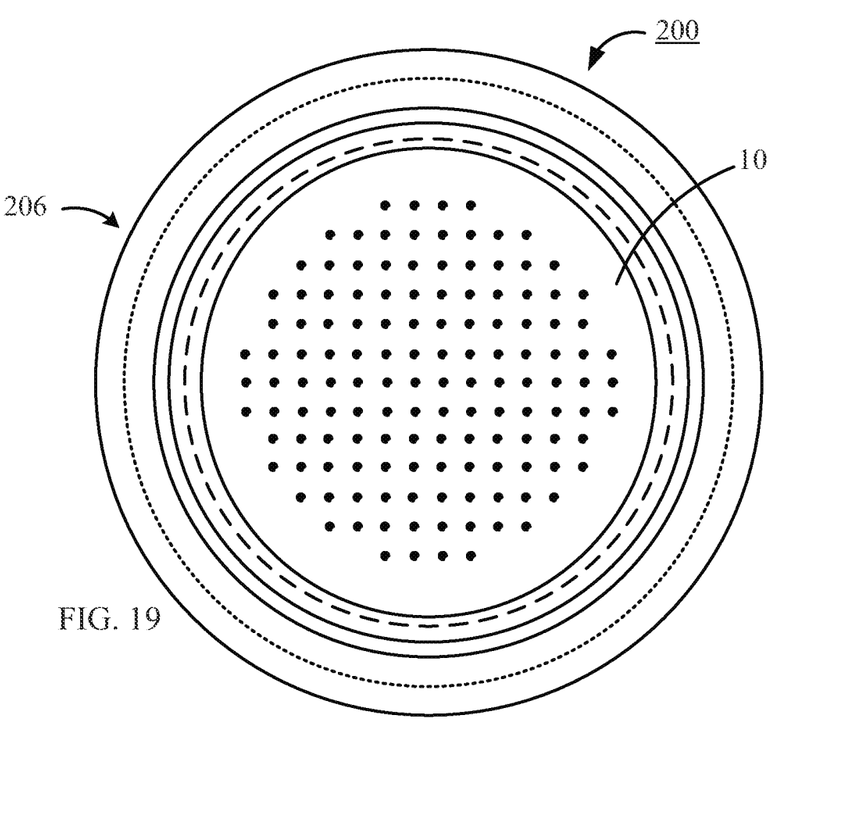
FIG. 19 is a bottom plan view of the novel sensor assembly of FIG. 18.

FIG. 19 shows the preferred embodiment of the sensor assembly 200 to be of a continuous curvilinear configuration, however, those skilled in the arts will recognize that any geometric shape may be presented by the sensor assembly 200. It is further noted that the sensor probe assembly 10, is confined by the housing 206 in such a manner that the sensor probe assembly 10, can be replaced without the disassembly of the entire sensor assembly 200.

Figure 20:
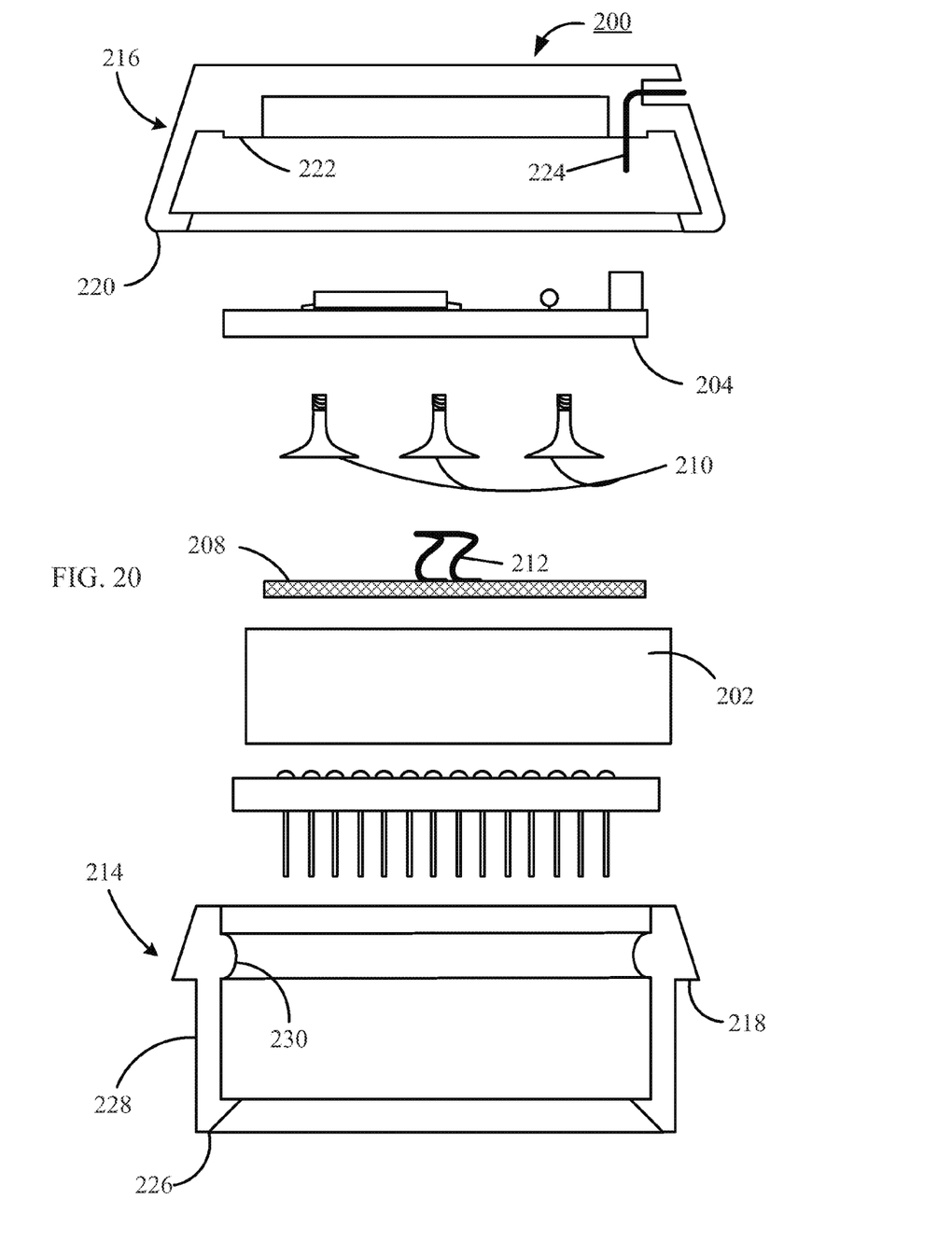
FIG. 20 is a front elevation view exploded view of the novel sensor assembly of FIG. 18.

The right side cross-section view and elevation of the preferred embodiment of the sensor assembly 200 of FIG. 20, reveals a rigid conductive member 208, and a plurality of standoffs 210, disposed between the signal processing circuit 204, and the electrically conductive member 202 (shown in its decompressed form). Preferably, the rigid conductive member 208 is in electrical interaction with a signal conductor 212, and the signal conductor 212 is in electrical communication with signal processing circuit 204. These standoffs 210, are preferably attached to the signal processing circuit 204, and function to provide a slight compressive load on the compressible electrically conductive member 202. The compressive load allows for decompression of the compressible electrically conductive member 202 while the probe assembly is being exchanged. This particular feature promotes stability of the rest of components within the housing 206, when the sensor probe assembly is absent from the remaining components of the sensor assembly 200.

As is further shown by FIG. 20, the housing 206, of FIG. 18, preferably includes a component chamber 214, and a confinement cover 216. The component chamber 214 preferably includes a confinement cover retention feature 218, which interacts with a retention member 220 of the confinement cover 216. In a preferred embodiment, the confinement cover 216 "snaps" onto the component chamber 214. In a preferred embodiment, the component chamber 214 and the confinement cover 216 are formed from a shape retaining material that provides sufficient flexibility to allow the retention member 220 of the confinement cover 216 to pass by the confinement cover retention feature 218 of the component chamber 214, and then lock together the confinement cover 216 with the component chamber 214. As those skilled in the art will recognize that there are a number of engineering materials suitable for this purpose including, but not limited to, metals, polymers, carbon fiber materials, and laminates.

In the preferred embodiment of the sensor assembly 200, the confinement cover 216 further includes at least a signal processing circuit retention feature 222 and a connector pin 224 supported by the signal processing circuit retention feature 222, while the component chamber 214 further includes at least: a sensor probe assembly retention feature 226; a side wall 228 disposed between the confinement cover retention feature 218 and the sensor probe assembly retention feature 226; and a holding feature 230 provided by the side wall 228 and adjacent in the confinement cover retention feature 218.

In the preferred embodiment of the sensor assembly 200, the compressibility of the compressible electrically conductive member 202 promotes an ability to change out the sensor probe assembly 10, without disturbing the interaction of the signal processing circuit 204 and the rigid conductive member 208, or to change out the processing circuit 204 and the rigid conductive member 208 without disturbing the sensor probe assembly 10. When the sensor probe assembly 10 is removed from the preferred embodiment of the sensor assembly 200, the compressible electrically conductive member 202 expands to interact with the sensor probe assembly retention feature 226 thus maintaining the rigid conductive number 208 in pressing contact with standoffs 210. When the signal processing circuit 204, standoffs 210, and the rigid conductive member 208 are removed from the preferred embodiment of the sensor assembly 200, the compressible electrically conductive member 202 expands to interact with the holding feature 230 to preclude the inadvertent removal of the sensor probe assembly 10 from communication with the sensor probes assembly retention feature 226.

As will be recognized by skilled artisans, it is the collaborative effect of the pin or pins 14 of the sensor probe assembly 10 interacting with the cranium of the subject that promotes transference of brainwave signals of the subject to the signal processing circuit 204. To promote the conveyance of the brainwave signal, the sensor probe assembly 10 further provides a conductive pin securement member 12 cooperating in retention contact with the plurality of conductive pins 14.

Figure 21:
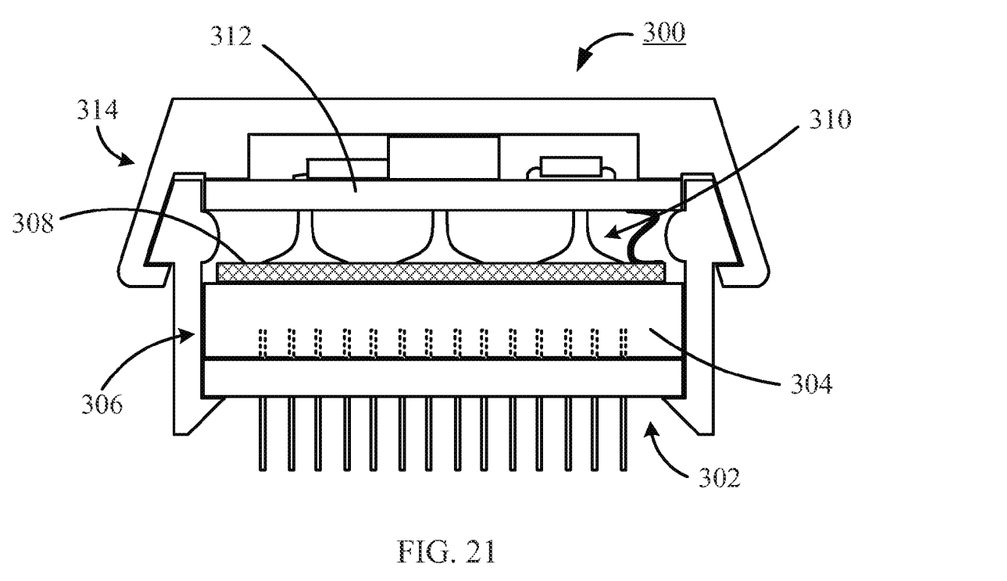
FIG. 21 is a front elevation view of an alternate embodiment exemplary of the present novel sensor assembly.

FIG. 21 shows an alternate preferred embodiment of a novel, inventive, standalone sensor assembly 300. Preferably, the standalone sensor assembly 300 includes at least an electrically conductive member 302 forming a first plate 304 of a capacitor 306, a dielectric material 308, adjacent the first plate 304, a second plate 310 of the capacitor 306 communicating with the dielectric material 308, and a signal processing circuit 312 in electrical communication with said dielectric material 308. FIG. 21 further shows a housing 314 confining the first plate 304 of the capacitor 306, the dielectric material 308, the second plate 310, and the signal processing circuit 312 to form the standalone sensor assembly 300.

Figure 22:
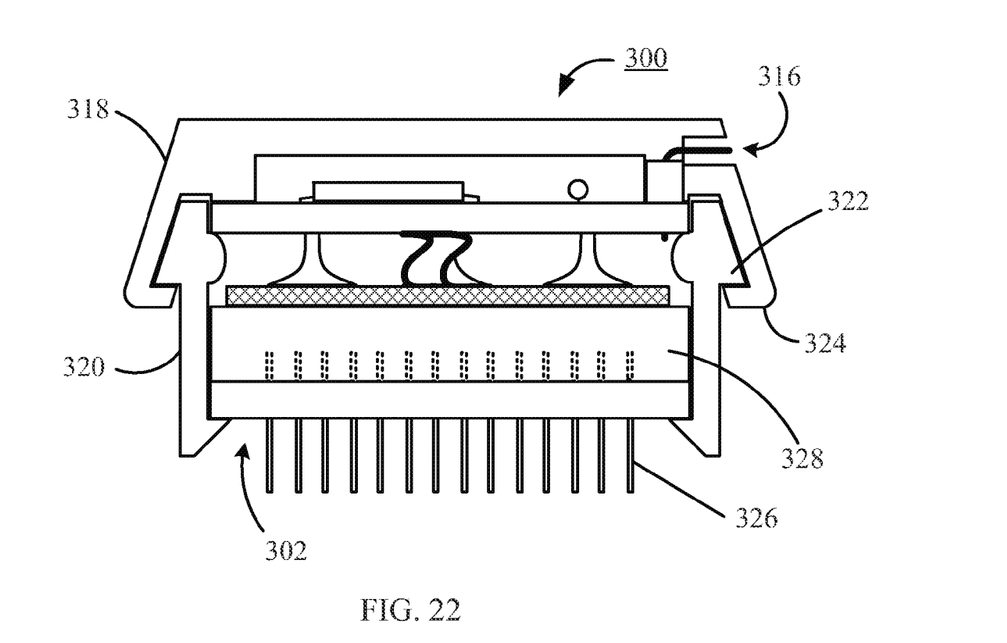
FIG. 22 is a side elevation view of an alternate embodiment exemplary of the present novel sensor assembly of FIG. 21.

FIG. 22 shows the standalone sensor assembly 300 further includes a communication port 316, useful for transferring processed signals to an external system for analysis, and that the housing 314 preferably includes a component chamber 318, and a confinement cover 320. The component chamber 318 preferably includes a confinement cover retention feature 322, which interacts with a retention member 324 of the confinement cover 320. In a preferred embodiment, the confinement cover 320 "snaps" onto the component chamber 318.

In a preferred embodiment, the component chamber 318 and the confinement cover 320 are formed from a shape retaining material that provides sufficient flexibility to allow the retention member 324 of the confinement cover 320 to pass by the confinement cover retention feature 322 of the component chamber 318, and then lock together the confinement cover 320 with the component chamber 318. As those skilled in the art will recognize that there are a number of engineering materials suitable for this purpose including, but not limited to, metals, polymers, carbon fiber materials, and laminates.

In a preferred embodiment, the electrically conductive member 302 forming the first plate 304 of the capacitor 306 includes at least, but is not limited to, a plurality of at least partially insulated pins 326, communicating with a conductive member 328, wherein the conductive member is in direct contact adjacency with the dielectric material 308. The plurality of at least partially insulated pins 326, each preferably have four degrees of freedom i.e.: yaw; pitch; roll; and z axis. The multiple degrees of freedom accommodates the topography differences in the cranium of different subjects, to promote a subject adaptable, alternate preferred embodiment of the novel, inventive, standalone sensor assembly 300.

Figure 23:
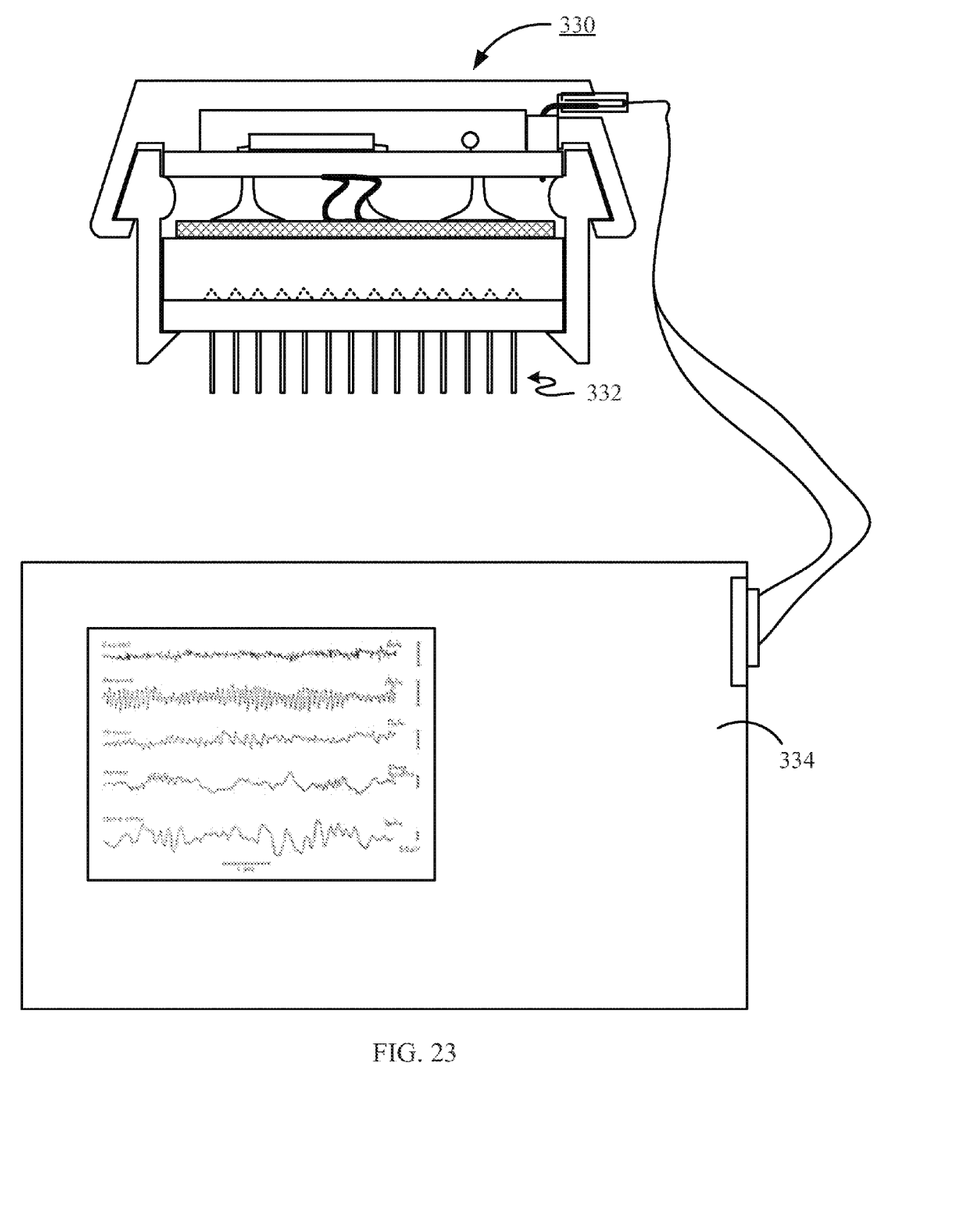
FIG. 23 is a side elevation view of an alternate embodiment exemplary of the present novel sensor assembly of FIG. 21, communicating with a brainwave processing system.

FIG. 23 shows an alternative preferred embodiment of the novel, inventive, standalone sensor assembly 330, having a plurality of alternate conductive pins 332; however, the remaining components are substantially equal to the corresponding remaining components of the preferred embodiment of the novel, inventive, standalone sensor assembly 200. Further shown by FIG. 23, is a brainwave processing system 334, which may be, for example, an Electroencephalography (EEG) 334.

Figure 24:
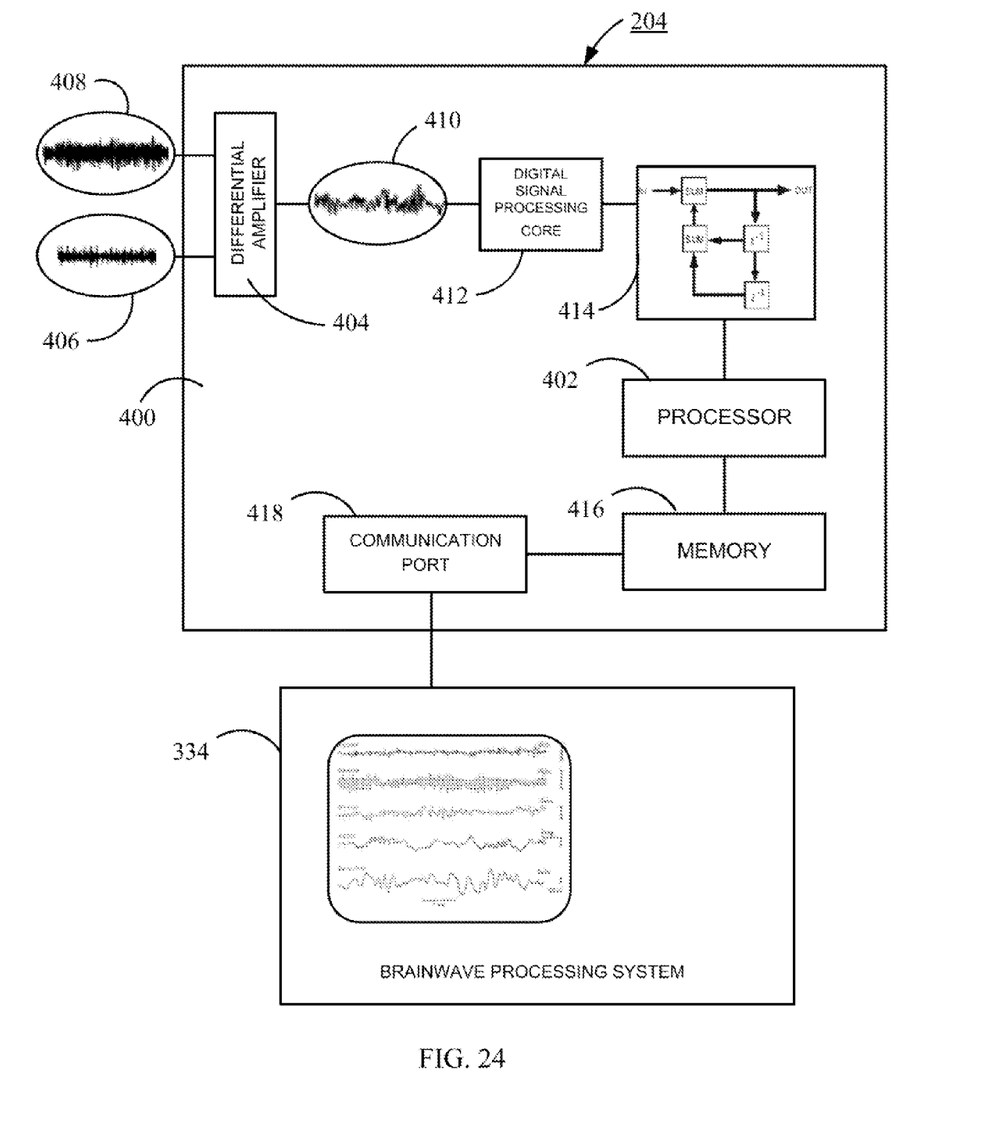
FIG. 24 is a schematic of a preferred signal processing circuit of the embodiment exemplary of the present novel sensor assembly of either FIG. 18, 21, or 23.

As is shown by FIG. 24, a preferred embodiment of the signal processing circuit 204 includes at least, but is not limited to, a printed circuit member 400, and a processor 402, interacting with said printed circuit member 400, the processor receiving signals from a sensor probe assembly, such as 200 of FIG. 18, and communicating the signals to a brainwave processing system, such as 334 of FIG. 23.

The preferred embodiment of the signal processing circuit 204 further includes at least, but is not limited to, a differential amplifier 404, interacting with the printed circuit member 400, a reference signal 406 communicating with the differential amplifier 404, and a subject signal 408 provided by a sensor probe assembly, such as 200 of FIG. 18, when the sensor probe assembly 200 is in electrical contact with a cranium of a subject. Preferably, the differential amplifier 404 compares the reference signal 406 to the subject signal 408 and discards common signal patterns presented by said reference and subject signals, 404 and 406, to provide a native brainwave signal 410, of the subject.

Further, the preferred embodiment of the signal processing circuit 204 includes at least, but is not limited to, an analog to digital converter with a digital signal processing core 412, interacting with the differential amplifier 404 and processing the native brainwave signal 410, provided by the differential amplifier 404, and outputting a digital signal representative of the native brainwave signal, and an infinite impulse response filter 414, interacting with the analog to digital converter 412, to serve as a band pass filter for said digital signal.

Still further, the preferred embodiment of the signal processing circuit 204 shown in FIG. 24, includes at least, but is not limited to, a memory 416, also referred to herein as a buffer 416, communicating with the processor 402, and storing processed native brainwave signals, and a communication port 418 communicating with the buffer 416, the communication port is preferably responsive to the processor 402 for communicating processed native brainwave signals to the brainwave processing system 334.

Figure 25:
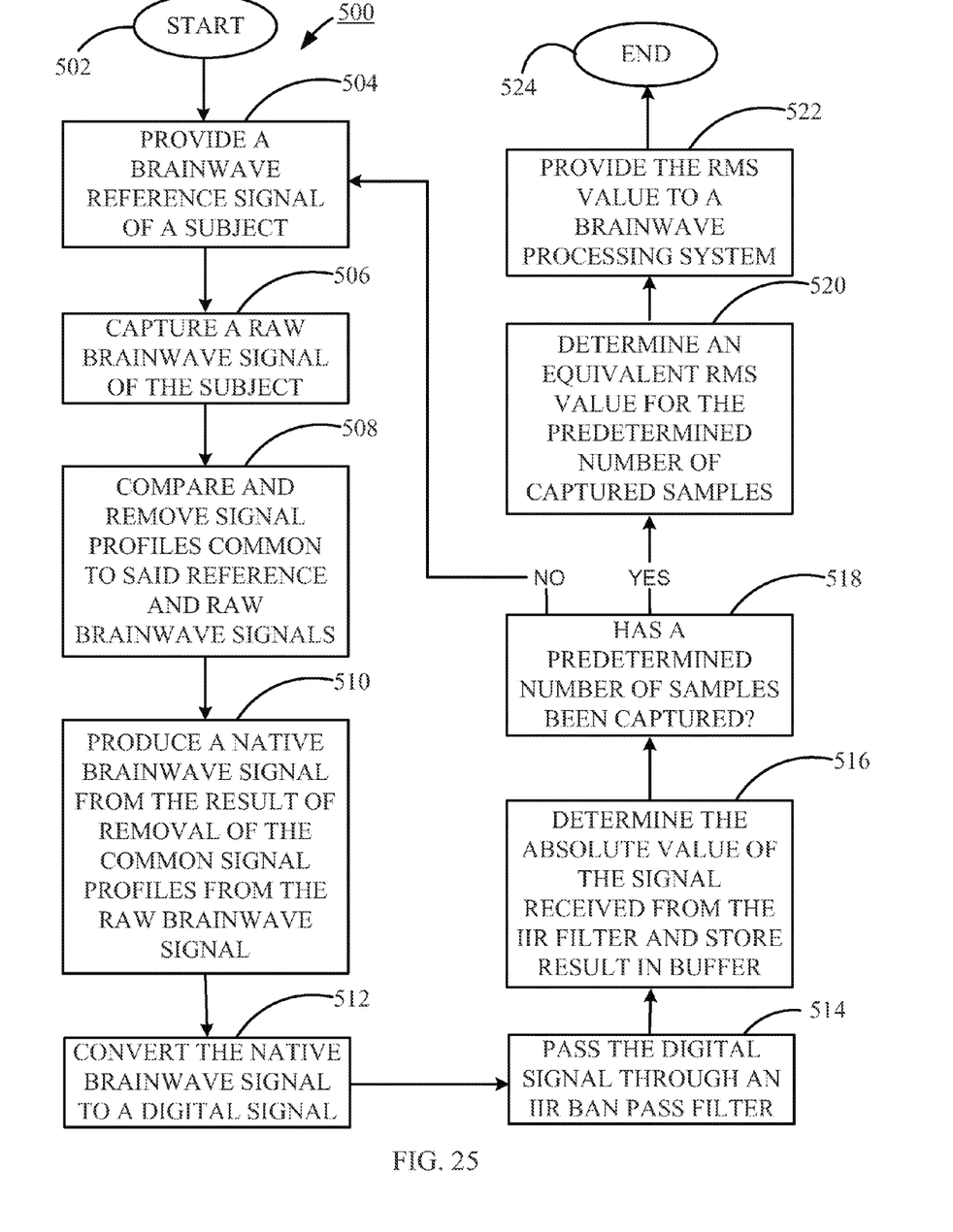
FIG. 25 is a flowchart of a method of using an embodiment exemplary of the inventive sensor assembly of either FIG. 18, 21, or 23.

FIG. 25 shows a method 500, of using a signal processing circuit, such as 400, of FIG. 24. The method begins at start step 502, and proceeds to process step 504, where a brainwave reference signal (such as 406) of a subject is provided. At process step 506, a raw brainwave signal (such as 408) of the subject is captured. At process step 508, the signal profiles of the reference and raw brainwave signals are compared, and signal profiles common to both are removed, and at process step 510, a native brainwave signal (such as 410) is produced from the result of the removal of signal profiles common to both the reference and raw brainwave signals.

The process continues at process step 512, where the native brainwave signal is converted to a digital band of frequency signal, and passed to an IIR ban pass filter (such as 414) at process step 514. At process step 516, an absolute value of the digitized signal received from the IRR filter is determined by a processor (such as 402). It is noted that in a preferred embodiment the IIR filter is programmable and responsive to the processor, and that multiple IIR filters may be employed to capture a multitude of discrete ban frequencies (typically having about a 5 Hz spread, such as 10 to 15 Hz out of a signal having a frequency range of about 0.5 Hz to 45 Hz)), or the programmable IIR filter may be programmed to collect a certain number of discrete, common frequency band samples, each sample obtained over a predetermined amount of time, and then reprogrammed to obtain a number of different, discrete, common frequency band samples.

The process continues at process step 518, where the processor determines if a predetermined number of samples of the absolute value each discrete band frequency of interest has been stored in a buffer (such as 416). If the number of captured desired samples has not been met, the process reverts to process step 504. If the number of captured desired samples has been met, the process proceeds to process step 520. At process step 520, the processor determines an equivalent RMS (root mean square) value for each of the plurality of discrete band frequency, absolute value sets of samples, and those values are provided to a brainwave processing system (such as 334) at process step 522. At process step 524, the process ends.

As will be apparent to those skilled in the art, a number of modifications could be made to the preferred embodiments which would not depart from the spirit or the scope of the present invention. While the presently preferred embodiments have been described for purposes of this disclosure, numerous changes and modifications will be apparent to those skilled in the art. Insofar as these changes and modifications are within the purview of the appended claims, they are to be considered as part of the present invention.

What is claimed is:

1. A sensor assembly comprising;
a sensor probe assembly providing a plurality of conductive pins;
a compressible electrically conductive member in electrical communication with the sensor probe assembly;
a signal processing circuit in electrical communication with the compressible electrically conductive member; and
a housing confining said sensor probe assembly, and the compressible electrically conductive member, wherein the electrically conductive member is formed from a polymer filled with conductive particles, said signal processing circuit is confined by said housing, and in which said sensor probe assembly further provides a pin securement member cooperating in retention contact with the plurality of conductive pins.

2. The sensor assembly of claim 1, further comprising a rigid conductive member with a signal conductor affixed thereon, said rigid conductive member in pressing contact with said compressible electrically conductive member, and said signal conductor communicating signals from said plurality of conductive pins to said signal processing circuit.

3. The sensor assembly of claim 1, further comprising a standoff disposed between said signal processing circuit and said compressible electrically conductive member, said standoff providing a predetermined compressive load on said compressible electrically conductive member.

4. The sensor assembly of claim 1, further comprising a communication port interacting with said signal processing circuit and communicating information between said signal processing circuit and a brainwave processing system.

5. The sensor assembly of claim 1, wherein the conductive particles comprise carbon, and wherein the pin securement member is a flexible electrically conductive member of predetermined impedance when in the circuit cooperating with the plurality of conductive pins.

6. The sensor assembly of claim 1, in which the polymer is polyurethane.

7. The sensor assembly of claim 6, wherein the conductive particles comprise carbon.

8. The sensor assembly of claim 1, in which said housing comprises a component chamber cooperating with a confinement cover, said component chamber supporting said sensor probe assembly, and said compressible electrically conductive member, and said confinement cover confining said sensor probe assembly, and said compressible electrically conductive member.

9. The sensor assembly of claim 8, in which said component chamber comprising:
   a confinement cover retention feature interacting with a retention member of the confinement cover;
   a sensor probe assembly retention feature communicating with the sensor probe assembly to retain the sensor probe assembly in a predetermined position; and
   a side wall disposed between said confinement cover retention feature and said sensor probe assembly retention feature, wherein said side wall provides a holding feature adjacent the confinement cover retention feature, said holding feature precluding an inadvertent removal of said compressible electrically conductive member and sensor probe assembly from communication with said sensor probe assembly retention feature.

10. The sensor assembly of claim 9, in which said confinement cover comprising:
    the retention member interacting with the confinement cover retention feature to secure the component chamber adjacent stud confinement cover;
    a signal processing circuit retention feature in pressing contact with said signal processing circuit; and
    at least one connector pin communicating with the retention member and electrically interacting with the signal processing circuit.

11. The sensor assembly of claim 1, in which said signal processing circuit comprising:
    a printed circuit member interacting with a standoff disposed between a signal processing circuit and said compressible electrically conductive member, said standoff providing a predetermined compressive load on said compressible electrically conductive member; and
    a processor interacting with said primed circuit member, said processor receiving signals from said sensor probe assembly and communicating said signals to a brainwave processing system, in which said signal processing circuit is confined by said housing.

12. The sensor assembly of claim 11, in which the signal processing circuit further comprising:
    differential amplifier interacting with said printed circuit member;
    a reference signal communicating with said differential amplifier; and
    a subject signal provided by said sensor probe assembly, when said sensor probe assembly is in electrical contact with a cranium of a subject, wherein said differential amplifier compares said reference signal to said subject signal and discards common signal patterns presented by said reference and subject signals to provide a native brainwave signal of the subject.

13. The sensor assembly of claim 12, in which the signal processing circuit further comprising:
    an analog to digital converter with a digital signal processing core interacting with said differential amplifier and processing said native brainwave signal provided by said differential amplifier and outputting a digital signal representative of said native brainwave signal; and
    an infinite impulse response filter interacting with said analog to digital converter to serve as a band pass filter for said digital signal.

14. The sensor assembly of claim 12, in which the signal processing circuit further comprising:
    a memory communicating with said processor and storing a plurality of native brainwave signals; and
    a communication port communicating with the memory and responsive to the processor for communicating native brainwave to the brainwave processing system.

\* \* \* \* \*